(12) United States Patent
Burkhardt et al.

(10) Patent No.: US 6,221,331 B1
(45) Date of Patent: Apr. 24, 2001

(54) METHOD OF SYNTHESIS OF LITHIUM SUBSTITUTED BOROHYDRIDE REAGENTS AND METHOD OF SYNTHESIS OF REACTIVE LITHIUM HYDRIDE

(75) Inventors: Elizabeth R. Burkhardt, Bridgeville; Christopher P. Sutton, Mars; Joerg Bruening, Allison Park; David F. Rouda, Renfrew, all of PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 0 days.

(21) Appl. No.: 09/490,982

(22) Filed: Jan. 24, 2000

Related U.S. Application Data

(62) Division of application No. 09/318,415, filed on May 25, 1999.

(51) Int. Cl.⁷ .................... C01B 6/04; C01B 4/00
(52) U.S. Cl. ...................... 423/646; 423/647.7
(58) Field of Search .................. 423/646, 647.7

(56) References Cited

U.S. PATENT DOCUMENTS 3,271,108 * 9/1966 Fujioka .
4,605,547 * 8/1986 Dumousseau et al. .

OTHER PUBLICATIONS

CA:89:196727 abs of Acta Chem Scand. Ser. B., B(32) pp 162–6, 1978.*
CA:105:133107 abs of J Am Chem Soc by Kowalski et al 108(17) pp 5356–7, 1986.*
Klusener et al in Angewandte Chemie ( international Edition) vol. 25, No. 5 pp 465–466, Oct. 1986.*

Andres, H. et al.: "preparation and use of superactive tritides" Synthesis and Applications of Isotopically Labelled Compounds, 1991, pp. 40–45, XP000929451 cited in the application the whole document.

Screttas, C. G., et al.: "solvent effects in organometallic reactions. vi. a kinetic role of base" Journal of The Americal Chemical Society vol. 88, No. 23, 1966, pp. 5668–5670, XP002143414 cited in the application, p. 5669, Eq. 6.

Klusener, P.A.A. et al.: "superactive alkali metal hydride metalation reagents: lih, nah, and kh" vol. 25, No. 5, 1986, pp. 465–466, XP002143415 the whole document.

* cited by examiner

Primary Examiner—Jean F. Vollano
(74) Attorney, Agent, or Firm—J. G. Uber; H. E. Bartony, Jr.

(57) ABSTRACT

A synthetic route for forming lithium trisubstituted borohydride compounds comprises the step of reacting a processed lithium hydride reactant with a trisubstituted borane wherein the reaction is maintained for a period of time in a temperature range of approximately 15° C. to approximately 42° C. A method of synthesizing LiH comprises the step of reacting an alkyl lithium (for example, n-butyl lithium) with hydrogen in the presence of tetrahydrofuran. The reaction temperature is preferably maintained in the range of approximately −78° C. to approximately 25° C.

20 Claims, 2 Drawing Sheets

"Unhindered" Trialkylboranes eg. triethylborane triisobutylborane

---

"Hindered" Trialkylboranes tricyclopentylborane

B-hexyl-9-borabicycl0[3.3.1]nonane tri-sec-butylborane

B-cyclohexyl-9-borabicycl0[3.3.1]nonane tricyclohexylborane

Highly Hindered Trialkylboranes

Alpine-Borane® tri(trans-2-methylcyclopentyl)borane trisiamylborane

METHOD OF SYNTHESIS OF LITHIUM SUBSTITUTED BOROHYDRIDE REAGENTS AND METHOD OF SYNTHESIS OF REACTIVE LITHIUM HYDRIDE

This is a divisional of copending application Ser. No. 09/318,415 filed on May 25, 1999.

FIELD OF THE INVENTION

The present invention relates to a method of synthesis of lithium substituted borohydride reagents and to a method of synthesis of lithium hydride, and, more particularly, to a method of synthesis of sterically hindered lithium substituted borohydride reagents and to a method of synthesis of lithium hydride from an alkyl lithium compound in the presence of tetrahydrofuran.

BACKGROUND OF THE INVENTION

Since the early 1970's there has been a strong interest in synthesizing alkali metal trisubstituted borohydride reagents because of their unique reactivity and synthetic utility in organic chemistry. Lithium trisubstituted borohydrides reagents, for example, are used in organic synthesis primarily as regioselective and stereoselective borohydride reducing agents. Most preparations of lithium trisubstituted borohydrides have focused on the reaction of lithium hydride or lithium aluminum reagents and trialkyl boranes to produce the above mentioned compounds. The reaction formula below represents the reaction of lithium hydride and a trisubstituted borane.

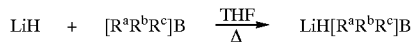

Unfortunately, there has been little success in synthesizing sterically hindered lithium trisubstituted borohydride reagents from commercially available lithium hydride and corresponding sterically hindered trisubstituted boranes. Indeed, a number of investigators have noted that hindered and highly hindered trisubstituted boranes are essentially inert towards lithium hydride. See, for example, Brown, H. C. et al., *J. of Organometallic Chem.*, 166, 27–280 (1979); Brown, H. C. et al., *J. of Organometallic Chem.*, 188, 1–10 (1980); Brown, H. C., *Tetrahedron*, 37, 2359–2362 (1981); and Thompson, et al., *J. Org. Chem.*, 44:26, 5004–5005 (1979).

It is believed that processed or commercially available lithium hydrides are not highly reactive in such reactions. Even with special washing and activating procedures, sterically hindered trisubstituted borohydrides (for example, lithium tri-sec-butylborohydride) cannot be produced in commercially viable yields from commercially available lithium hydrides. See, Hubbard, J. L., Tet. Let., 29, No. 26 3197–3200 (1988). In that regard, the yields from such reactions are less than 10% in 24 hours based upon the amount of the limiting reagent consumed in the reaction.

There are some indication that lithium hydride (LiH) formed in situ, may be more reactive toward sterically hindered substituted boranes than commercially available LiH. For example, it is known that n-butyl lithium slowly thermally decomposes by evolution of 1-butene and precipitation of LiH. *J. Org. Chem*, 30, 4138 (1965). The generation of LiH from n-BuLi is more efficient by hydrogenation of n-BuLi in the presence of tetramethylethylenediamine (TMEDA). *J. Am. Chem. Soc.*, 60, 2336 (1938); *J. Am. Chem. Soc.*, 88, 5668 (1966); and *J. Am. Chem. Soc.*, 52, 4299 (1987). One literature report indicated that LiH produced by this method with one equivalent of TMEDA was of sufficient reactivity to react with tri-sec-butylborane to generate lithium tri-sec-butylborohydride. Andres, H., *Synthesis and Applications of Isotopically Labeled Compounds*, 40–45 (1991); and 83–90, (1994). The present inventors have discovered, however that TMEDA, even when used in catalytic amounts, imparts impurities in the lithium trialkylborohydride which are detrimental to intended usage.

It is very desirable, therefore, to develop commercially viable methods of producing sterically hindered lithium substituted borohydride reagents that do not suffer from the problems associated with current synthetic routes.

SUMMARY OF THE INVENTION

The present invention provides a method of synthesizing sterically hindered lithium tri-substituted compounds (for example, compounds having the formula Li[R$^1$R$^2$R$^3$B]H, wherein R$^1$, R$^2$ and R$^3$, are independently, the same or different). As used herein, the phrase "hindered lithium trisubstituted borohydride compounds" refers generally to sterically hindered compounds wherein the boron atom is attached to a secondary carbon or a tertiary carbon on at least two of substituents R$^1$, R$^2$ and R$^3$. If the boron is attached to two substituents via tertiary carbons, the third substituent should be attached to the boron via a primary carbon. Neither of the two substituents attached to the boron atom via a tertiary carbon should be substituted at the α-carbon. As used herein, the term α-carbon refers to the carbon adjacent the carbon attached to the boron. If the boron is attached to two substituents via secondary carbons, the third substituent may be attached to the boron via a secondary carbon or a primary carbon. If all three substituents are attached to the boron via secondary carbons, none of the substituents should be substituted at the α-carbon. If two of the three substituents are attached to the boron via secondary carbons, one of these substituents can be substituted at the α-carbon. Lithium tri-substituted compounds that are more hindered than those described above are considered to be "highly" hindered.

R$^1$, R$^2$ and R$^3$ can, for example, be independently alkyl or aryl groups. In one embodiment, the substituents are alkyl groups (for example, unbranched, branched, cyclic or acyclic secondary alkyl groups). Specific examples, of tri-sec-alkylborohydride compounds synthesized via the present method include lithium tri-sec-butylborohydride, lithium B-hexyl-9-boratabicyclo[3.3.1]nonane and lithium B-cyclohexyl-9-boratabicyclo[3.3.1]nonane.

In general, the method comprises the step of reacting lithium hydride and a sterically hindered trisubstituted borane in a reaction vessel to produce the hindered lithium trisubstituted borohydride compound. As used herein, the terms "lithium hydride or LiH" encompass isotopes including LiH (wherein lithium is bonded to hydrogen), LiD (wherein lithium is bonded to deuterium) and LiT (wherein lithium is bonded to tritium). The reaction temperature is preferably maintained in a temperature range of approximately 15° C. to approximately 42° C. during a period of time. The period of time is preferably at least approximately 20 minutes. More preferably, the reaction is maintained in a temperature range of approximately 20° C. to approximately 35° C. for a period of time. Even more preferably, the reaction is commenced in a temperature range of approximately 15° C. to approximately 42° C. Still more preferably, the reaction is commenced in a temperature range of approximately 20° C. to 35° C.

Preferably, the lithium hydride and the trisubstituted borane substrate are of relatively high purity. In that regard, the purity of the lithium hydride is preferably at least approximately 80%. More preferably, the purity of the lithium hydride is at least approximately 95%. Most preferably, the purity of the lithium hydride is at least approximately 98%. The purity of the trisubstituted borane is preferably at least approximately 85% relative to other boron species. More preferably, the purity of the trisubstituted borane is at least approximately 90%. Most preferably, the purity of the trisubstituted borane is at least approximately 95%. Tetrahydrofuran is preferably used as a solvent for the reaction. In a preferred embodiment, the lithium substituted borohydride product is lithium tri-sec-butylborohydride.

The present inventors have discovered that yields of sterically hindered lithium trisubstituted borohydrides in excess of 10% (in 24 hours based upon the limiting reagent in the reaction) can be achieved in the present method with lithium hydride reactants with which such yields were not previously possible. Indeed, commercially viable yields of such hindered lithium trisubstituted borohydrides are possible in the present invention with processed lithium hydride reagents, which include all commercially available lithium hydrides. As used herein, the phrase "processed lithium hydride reagent" refers generally to lithium hydride reagents that have been subjected to processing such as particle size reduction or removal of a liquid reaction matrix. Such processing reduces the reactivity of such reagents, possibly as a result of even very limited exposure to ambient atmospheric conditions. Typically, such lithium hydride reagents have been isolated as powders. The present invention thus also provides a method of improving the yield of a reaction of a processed lithium hydride reactant and a sterically hindered trisubstituted borane to produce a hindered lithium trisubstituted borohydride compound comprising the step of maintaining the reaction temperature in a range of approximately 15° C. to approximately 42° C. during a period of time.

Preferably, the yield of such a reaction is improved to greater than 10% based upon the amount of limiting reagent consumed in the reaction. More preferably, the yield is improved to greater than 25%. Even more preferably, the yield is improved to greater than 50%. Most preferably, the yield is improved to greater than 75%.

The present invention also provides a method of synthesizing lithium hydride, LiD or LiT comprising the step of reacting an alkyl lithium (preferably, n-butyl lithium) with hydrogen, deuterium or tritium in the presence of tetrahydrofuran. The reaction temperature is preferably maintained in the range of approximately −78° C. to approximately 20° C. More preferably, the reaction temperature is maintained in the range of approximately −30° C. to approximately 0° C. Even more preferably, the reaction temperature is maintained in the range of approximately −20° C. to approximately 0° C. Most preferably, the reaction temperature is maintained in the range of approximately −15° C. to approximately −50C. Preferably, no catalyst (for example, an amine catalyst such as TMEDA) is present in the reaction.

Preferably, the tetrahydrofuran and alkyl lithium are chilled below room temperature when added together into a reactor. Preferably chilled tetrahydrofuran is added to a chilled alkyl lithium. The tetrahydrofuran is preferably chilled to a temperature in the range of approximately −78° C. to approximately 20° C. More preferably, the tetrahydrofuran is chilled to a temperature in the range of approximately −30° C to approximately 0° C. Even more preferably, the tetrahydrofuran is chilled to a temperature in the range of approximately −20° C. to approximately 0° C. Most preferably, the tetrahydrofuran is chilled to a temperature in the range of approximately −15° C. to approximately −5° C.

In the case of 10M n-butyl lithium, the n-butyl lithium is preferably chilled to a temperature in the range of approximately −10° C. to approximately 0° C. before addition thereof. At lower concentrations of n-butyl lithium, the n-butyl lithium can be chilled to a lower temperature.

The present invention also provides a method of synthesizing a lithium trisubstituted borohydride compound having the formula $Li[R^4R^5R^6B]H$, wherein $R^4$, $R^5$ and $R^6$ are, independently, the same or different, an alkyl group, an aryl group, an alkoxyl group, or an aryloxyl group. AS discussed above, H can be substituted with D or T and the formula $Li[R^4R^5R^6B]H$ included theses variations. The method generally comprises the steps of: (a) synthesizing LiH, LiD or LiT by reacting an alkyl lithium (preferably, n-butyl lithium) with hydrogen, deuterium or tritium in the presence of tetrahydrofuran, the reaction temperature being maintained in the range of approximately −78° C. to approximately 20° C. (that is, under the reaction conditions discussed above); and (b) reacting the LiH, LiD or LiT and a trisubstituted borane having the formula $R^4R^5R^6B$ in a reaction vessel to produce the lithium trisubstituted borohydride compound.

Given the highly reactive nature of the in situ LiH of the present invention, the trisubstituted borane can be sterically hindered or highly sterically hindered. For example, any or all of $R^4$, $R^5$ and $R^6$ can be a secondary alkyl group, an -substituted secondary group or a tertiary alkyl group.

During the step of reacting the LiH and the trisubstituted borane, the reaction temperature is preferably maintained below approximately 55° C. In a preferred embodiment, the trisubstituted borane is tri-sec-butylborohydride.

As used herein, the term "alkyl group" refers preferably to $C_1$–$C_{18}$ alkyl groups and, more preferably, to $C_2$–$C_{12}$ alkyl groups. The alkyl groups can be normal, branched or cyclic. As used herein, the term "aryl group" refers preferably to phenyl and napthyl groups. As used herein, the term "alkoxyl group" refers preferably to groups having the formula —$OR^7$, wherein $R^7$ is preferably an alkyl group as defined above. As used herein, the term "aryloxyl group" refers preferably to groups having the formula —$OR^8$, wherein $R^8$ is preferably an aryl group as defined above.

The various alkyl, aryl, alkoxyl, and aryloxyl groups discussed above can be substituted or unsubstituted. If substituted, such groups are preferably substituted with unreactive substituents. In that regard, the substituent groups are preferably compatible with the borohydride materials. Because of the reactive nature of the borohydride materials, such substituents are somewhat limited and typically include alkyl groups, aryl groups, arylalkyl groups, alkoxyl groups, aryloxyl groups, arylthio groups, dialkylamino groups, diarylamino groups, dialkylphosphino groups and diarylphosphino groups. See for example, U.S. Pat. No. 4,082,810 for a discussion of such groups.

DETAILED DESCRIPTION OF THE INVENTION

Figure 1:
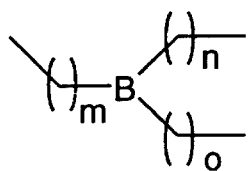
FIG. 1 illustrates several examples of unhindered and hindered trisubstituted boranes.
Figure 1:
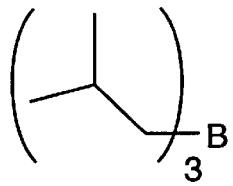
Figure 1:
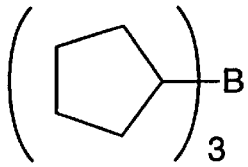
Figure 1:
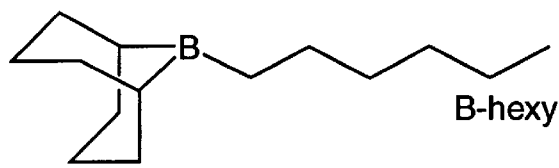
Figure 1:
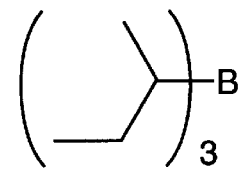
Figure 1:
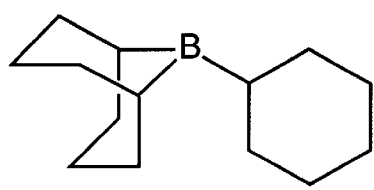
Figure 1:
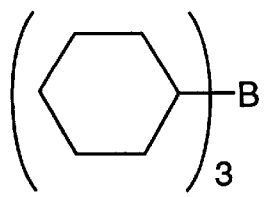
Figure 2:
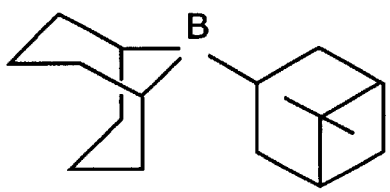
FIG. 2 illustrates several examples of highly hindered tri-substituted boranes.
Figure 2:
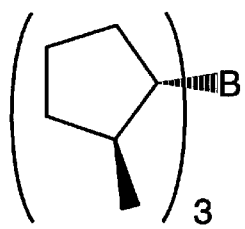
Figure 2:
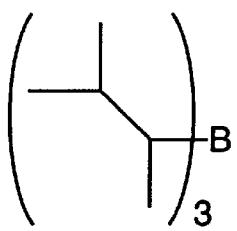

The present invention provides processes for the commercial/industrial production of sterically hindered and other lithium substituted borohydride reagents via the reaction of commercially available or in situ prepared lithium hydride and a substituted borane. Examples of unhindered, hindered and highly hindered trisubstituted borohydride compounds (as such terms are defined above) are illustrated in FIGS. 1 and 2.

Synthesis of Sterically Hindered Trisubstituted Borohydride Reagents from Commercially Available Lithium Hydride In a number of studies, the reaction of lithium hydride with tri-sec-butylborane (TSBB) to produce lithium tri-sec-butylborohydride was used as a model reaction according to the following formula:

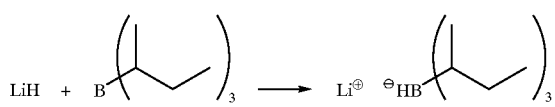

In contrast to the numerous literature references, the present inventors have discovered that commercial lithium hydride is capable of reacting with tri-sec-butylborane, producing lithium tri-sec-butylborohydride in moderate to high yields.

Table 1 sets forth a summary of 14 separate experiments in which lithium tri-sec-butylborohydride was successfully prepared in greater than 80% yield via reaction of tri-sec-butylborohydride with commercial LiH under the conditions of the present invention.

TABLE 1

| Experiment | Reactor | LiH [g], mol | TSBB [g], mol | THF [ml] | Feed time/ Feed temp. | Time to Temp. | Rxn. time/ Rxn temp. | Yield (%, $^{11}$B-NMR) |
|---|---|---|---|---|---|---|---|---|
| 1-1 | Parr | 2.39, 0.3 mol | 54.65 0.3 mol | 250 | 10 min/22° C. | 25 min | 23 h/52° C. | 80.4 |
| 1-2 | Parr | 2.39 g, 0.3 mol | 54.65 0.3 mol | 250 | <1 min/23° C. | 15 min | 18 h/35° C. 25 h/35° C. | 77.3 83.5 |
| 1-3 | Morton Flask | 3.14 g, 0.375 mol | 54.65 0.3 mol | 250 | <1 min/34° C. | 0 | 18 h/34° C. 24 h/34° C. | 85.5 86.3 |
| 1-4 | Parr | 3.14 g, 0.375 mol | 54.65 0.3 mol | 250 | 2 min/23° C. | 0 | 18 h/24° C. 24 h/24° C. | 79.2 83.8 |
| 1-5 | Parr | 5.02 g, 0.6 mol | 54.65 0.3 mol | 250 | <1 min/23° C. | 0 | 18 h/24° C. 24 h/24° C. | 89.8 91.0 |
| 1-6 | Zipperclave | 31.57 g 3.97 mol | 578.54 g 3.176 mol | 2396 | 43 min/23° C. | 25 min | 20 h/33–35° C. | 86.2 |
| 1-7 | Zipperclave | 31.57 g 3.97 mol | 578.54 g 3.176 mol | 2396 | 46 min/23° C. | 40 min | 4 h/35° C. 21 h/35° C. | 82.2 86.3 |
| 1-8 | Parr | 3.14 g 0.375 mol | 54.65 g 0.3 mol | 250 | 89 min/23° C. | 0 | 4.5 h/23–27° C. 21 h/23–27° C. | 82 84.8 |
| 1-9 | Parr | 2.39 g 0.3 mol | 54.65 g 0.3 mol | 250 | 30 sec/22° C. | 30 min r.t. 13 min | 22.3 h/35° C. | 86.6 |
| 1-10 | Parr | 2.39 g 0.3 mol | 54.65 g 0.3 mol | 250 | 78 min/23° C. | ca 30 min | overnight/35° C. | 86 |
| 1-11 | Parr | 2.98 g 0.375 mol | 54.65 g 0.3 mol | 250 | 13 min/22° C. | 12 min | 21 h/35 | 84 |
| 1-12 | Low P. Glass Reactor | 4.47 g 0.562 mol | 82 g 0.45 mol | 373 | 15 min/20° C. | | 3.5 h/20–36° C. 19 h/20–36° C. | 84 92 |
| 1-13 | Zipperclave | 31.57 g 3.97 mol | 578.54 g 3.176 | 2130 | 4.5 h/22–27° C. | 0 | 1.3 h/26° C. 19 h/27° C. | 81.7 83.1 |
| 1-14 | Low P. Glass Reactor | 4.47 g 0.562 mol | 82 g 0.45 mol | 373 | 15 min/21° C. | | 20 h/21–38° C. | 89 |

In the experiments the reaction yields were determined via integration of the TSBB and lithium tri-sec-butylborohydride signals in the $^{11}$B-NMR. This approach was validated using independent methods (that is total base/active hydride determination).

The inventors discovered that the temperature profile of the reaction has a significant impact on the reaction of LiH with TSBB yielding the lithium tri-sec-butylborohydride. Addition of TSBB at elevated reaction temperature 51–55° C. gave low conversion (0–18%), while addition of TSBB in a temperature range of approximately 20 to approximately 42° C. produced yields typically in the range of 60 to 86% lithium tri-sec-butylborohydride. At a reaction temperature of between 1–14° C., no conversion was observed within 24h. (Table 2: Experiment Nos. 2-1 to 2-9) It was also discovered that as long as the TSBB was allowed to react with the LiH in a temperature range of approximately 20° C. to approximately 42° C. for some period of time (for example, as little as 20 to 30 minutes), high yields of lithium tri-sec-butylborohydride could be obtained in experiments starting at a lower temperature or in experiments in which the reaction temperature was later raised above the initial temperature. (Table 2, Experiment Nos. 2-10 to 2-14).

TABLE 2

| Exp. No. | Reactor | LiH [g], mol | TSBB [g], mol | Feed. Time/ Feed temp. | Time to Temp. | Rxn. time/ Rxn temp. | Yield (%, $^{11}$B-NMR) |
|---|---|---|---|---|---|---|---|
| 2-1 | Parr | 2.39 g, 0.3 mol | 54.65 g 0.3 mol | 16 min/55° C. | 0 | 16.5 h/52 C. | 15.8 |
| 2-2 | Morton Flask | 3.14 g, 0.375 mol | 54.65 0.3 mol | <1 h/42° C. | 0 | 24 h/43 C. | 60.4 |
| 2-3 | Parr Lab 7 | 3.14 g, 0.375 mol | 54.65 g 0.3 mol | 1 min/34° C. | 0 | 1 h/35 C. 24 h/35 C. | 59.6 68.7 |
| 2-4 | Morton Flask | 3.14 g, 0.375 mol | 54.65 0.3 mol | <1 min/34° C. | 0 | 24 h/34 C. | 86.3 |
| 2-5 | Morton flask | 2.51 g, 0.3 mol | 62.85 g 0.345 mol | 1 min/31° C. | 0 | 24 h/30–37° C. | 72.9 |
| 2-6 | Morton Flask | 3.14 g, 0.375 mol | 54.65 0.3 mol | 1 min/23° C. | 0 | 24 h/r.t. | 72.7 |
| 2-7 | Parr | 3.14 g, 0.375 mol | 54.65 0.3 mol | 48 min/20° C. | 0 | 22 h/20–26° C. | 88.8 |
| 2-8 | Morton Flask | 3.14 g, 0.375 mol | 54.65 0.3 mol | 1 min/16° C. | 0 | 18 h/14° C. | 0 |
| 2-9 | Morton Flask | 3.14 g, 0.375 mol | 54.65 0.3 mol | <1 min/3–5° C. | 0 | 18 h/1–5° C. | 0 |
| 2-10 | Parr | 2.39 g, 0.3 mol | 54.65 g 0.3 mol | 1 min/24° C. | 30 min r.t. 30 min | 18 h/50° C., then 5 h/50° C.-r.t. | 78.3 |
| 2-11 | Parr | 2.39, 0.3 mol | 54.65 0.3 mol | 10 min/22° C. | 25 min | ca 19 h/52° C. 23 h/52° C. | 78.2 80.4 |
| 2-12 | Parr | 3.14 g, 0.375 mol | 54.65 g 0.3 mol | 1 min/24° C. | 40 min 30 min | 2 h/50° C. 17.5 h/50° C. | 23.6 79.3 |
| 2-13 | Parr | 2.39 g, 0.3 mol | 54.65 0.3 mol | 8 min/22° C. | 24 min | 17 h/61–50° C. | 68 |
| 2-14 | Morton Flask | 3.14 g, 0.375 mol | 54.65 0.3 mol | 1 min/16° C. | 15 min | ca.24 h/30–35° C. | 60.3 |

The purity of the reactants LiH and TSBB was found to be a factor in obtaining high yields of lithium tri-sec-butylborohydride. As illustrated in Table 3, low purity lithium hydride (for example, a purity of 77.7% by active hydrogen) as well as low purity tri-sec-butylborane (for example, a purity of 85% by $^{11}$B-NMR) resulted in relatively low conversion under standard conditions.

Preferably, therefore, the lithium hydride and the trialkyl borane substrate are of relatively high purity. In that regard, the purity of the lithium hydride is preferably at least approximately 80%. More preferably, the purity of the lithium hydride is at least approximately 95%. Most preferably, the purity of the lithium hydride is at least approximately 98%. The purity of the trialkyl borane is preferably at least approximately 85%. More preferably, the purity of the trialkyl borane is at least approximately 90%. Most preferably, the purity of the trialkyl borane is at least approximately 95%.

It is believed that the reactions of the present invention occur at or nearby the surface of the solid and not in the bulk solvent. This assumption is based on the at best marginal solubility of lithium hydride in common organic solvents. For example, the solubility of LiH in THF at room temperature was determined to be less than 0.00089 mol per liter. Consequently methods that increase or activate the surface lithium hydride particles toward reaction with trialkylboranes (for example, with tri-sec-butylborane) are anticipated to promote the desired reaction.

While, in theory, activation can be achieved via addition of additives, the present inventors discovered that physical methods such as, but not limited to, grinding of the lithium hydride, efficient or high shear stirring of the lithium hydride-solvent mixture or the lithium hydride-solvent-TSBB mixture, led to medium to high yields of lithium tri-sec-butylborohydride.

Reactions performed in reaction equipment with poor stirring/mixing (for example, round bottom flasks) typically

TABLE 3

| Experiment | LiH purity [% by active hydrogen] | LiH [g], mol | TSBB purity [by $^{11}$B-NMR] | TSBB [g], mol, | THF [ml] | Feed. Time/ Feed temp. | Rxn. time/ Rxn temp. | Yield (%, $^{11}$B-NMR) |
|---|---|---|---|---|---|---|---|---|
| Comparative example | | | | | | | | |
| 3-1 | 96.4 | 3.14 g 0.375 mol | >99.5 | 54.65 g 0.3 mol | 250 | 89 min/23° C. | 21 h/23–27° C. | 84.8 |
| 3-2 | 96.4 | 3.14 g 0.375 mol | 85 | 54.65 0.3 mol | 250 | 52 min/25° C. | overnight/27° C. | ca. 17 |
| Comparative example | | | | | | | | |
| 3-3 | 96.4 | 3.14 g 0.375 mol | >99.5 | 54.65 g 0.3 mol | 250 | 89 min/23° C. | 21 h/23–27° C. | 84.8 |
| 3-4 | 77.7 | 3.84 g 0.375 mol | >99.5 | 54.65 g 0.3 mol | 250 | 54 min/25° C. | overnight/25° C. | <3 | gave lower yields compared to reactions that were performed in equipment with good stirring/mixing (for example, Parr reactor). See Table 4. Also, it was discovered that extended stirring of the LiH/THF mixture before addition of the trialkylborane can lead to higher conversions (Table 5: Experiment Nos. 5-3 and 5-4).

conversion) without affecting the yield significantly. The lithium hydride to TSBB ratio was varied between approximately 0.5:1 to approximately 3:1 (Table 7, Experiment Nos. 7-1 to 7-5, 83% to 94% yield) without affecting the yield

TABLE 4

| Exp. No. | Reactor | LiH [g], mol | TSBB [g], mol | THF [ml] | Feed. Time/ Feed temp. | Time to Temp. | Rxn. time/ Rxn temp. | Yield (%, $^{11}$B-NMR) |
|---|---|---|---|---|---|---|---|---|
| Comparative example | | | | | | | | |
| 4-1 | Parr | 2.39, 0.3 mol | 54.65 g, 0.3 mol | 250 | 10 min/22° C. | 25 min | ca 19 h/52° C. 23 h/52° C. | 78.2 80.4 |
| 4-2 | Flask | 2.39 g, 0.3 mol | 54.65 g, 0.3 mol | 250 | 10 min/24° C. | ca 1 h | overnight/ 50° C. | 28.5 |
| 4-3 | Flask | 3.58 g, 0.45 mol | 54.65 g, 0.3 mol | 250 | ca. 10 min/24° C. | ca 1 h | overnight/ 48° C. | 27.7 |
| 4-4 | Flask | 7.16 g, 0.9 mol | 54.65 g, 0.3 mol | 250 | 10 min/23° C. | ca. 40 min | overnight 50° C. | 41.6 |
| Comparative example | | | | | | | | |
| 4-5 | Parr | 3.14 g, 0.375 mol | 54.65 g, 0.3 mol | 250 | 1 min/34° C. | 0 | 24 h/35° C. | 68.7 |
| 4-6 | Morton flask | 2.51 g, 0.3 mol | 62.85 g, 0.345 mol | 233 | 1 min/31° C. | 0 | 18 h/37° C. 24 h/30–38° C. | 60.7 72.9 |
| 4-7 | Morton Flask | 3.14 g, 0.375 mol | 54.65 g, 0.3 mol | 250 | <1 min/34° C. | 0 | 18 h/34° C. 24 h/34° C. | 85.5 86.3 |
| Comparative example | | | | | | | | |
| 4-8 | Parr | 3.14 g, 0.375 mol | 54.65 g, 0.3 mol | 250 | 89 min/23° C. | 0 | 21 h/23–27° C. | 84.8 |
| 4-9 | Morton Flask | 3.14 g, 0.375 mol | 54.65 g, 0.3 mol | 250 | 1 min/23° C. | 0 | 19 h/r.t. 24 h/r.t. | 72.7 72.7 |

TABLE 5

| Experiment | Pre-reaction Stirring of LiH/THF | LiH [g], mol, eq | TSBB [g], mol, eq | THF [ml] | Feed. Time/ Feed temp. | Rxn. time/ Rxn temp. | Yield (%, $^{11}$B-NMR) |
|---|---|---|---|---|---|---|---|
| 5-1 | 45 min @ r.t. | 3.14 g 0.375 mol | 54.65 g 0.3 mol 19.5 wt % | 250 | 1 min/34° C. | 1 h/35° C. 2 h/35° C. 3 h/35° C. 7 h/35° C. | 59.6 66.6 65.4 67.3 |
| 5-2 | 17 h @ 35° C. | 3.14 g 0.375 mol | 54.65 g 0.3 mol | 250 | 1 min/35° C. | 1 h/36° C. 2 h/36° C. 3 h/36° C. 7 h/36° C. | 51.8 59.6 60.2 63.1 |
| 5-3 | 45 min @ r.t. | 3.14 g 0.375 mol | 54.65 g 0.3 mol | 250 | 1 min/21° C. | 1 h/22° C. 2 h/22° C. 3.25 h/22–24° C. 4 h/22–24° C. 5 h/22–24° C. | 0 5 65.1 70.8 72.4 |
| 5-4 | overnight @ 50° C. | 3.14 g 0.375 mol | 54.65 g 0.3 mol | 250 | 89 min/23° C. | 1 h/23–26° C. 2.25/23–27° C. 3 h/23–27° C. 4.5 h/23–27° C. | 9.2 69.8 79.4 82 |

The present inventors also discovered that several reaction parameters can be significantly varied without causing substantial decreases in the yield of the lithium trialkyl borohydride (for example, lithium tri-sec-butylborohydride) in the method of the present invention.

For example, the reactant concentration was varied between approximately 20 and approximately 45wt % TSBB (Table 6, Experiment Nos. 6-1 to 6-8, 83% and 97% conversion) without affecting the yield significantly. The TSBB addition rate was varied between approximately 0.5 min and approximately 78 min at a given scale without affecting the yield significantly (Table 8, Experiment Nos. 8-1, 8-2). The order of addition of the reactants also -seemingly had no effect on the outcome of the reaction (Table 9, Experiment Nos. 9-3 and 9-4). Therefore, the more convenient mode of adding the TSBB to a slurry of LiH in THF was chosen.

TABLE 6

| Experiment | wt % TSBB in reaction mixture | LiH [g], mol | TSBB [g], mol | Feed. Time/ Feed temp. | Time to Temp. | Rxn. time/Rxn temp. | Yield (%, $^{11}$B-NMR) | Remarks |
|---|---|---|---|---|---|---|---|---|
| 6-1 | 21.1 | 31.57 g 3.97 mol | 578.54 g 3.176 mol | 43 min/23° C. | 25 min | 20 h/35° C. | 86.2 | liquid |
| 6-2 | 32.7 | 2.39 g 0.3 mol | 109.3 g 0.6 mol | <1 min/25° C. | 2.25 h/r.t. 15 min | 1.5 h/50° C. ca. 75 h/r.t.-50° C. | 65 94 | liquid |
| 6-3 | 34.7 | 5.96 g 0.75 mol | 109.3 g 0.6 mol | 6 min/21° C. | 1 h r.t. <50 min | ca. 18.5 h/35° C. | 83 | liquid |
| 6-4 | 44 | 5.96 g 0.712 mol | 109.3 g 0.6 mol | 28 min/24° C. | 2 h | ov/38–40° C. | ca. 80 | slush |
| 6-5 | 43.9 | 5.96 g 0.75 mol | 109.3 g 0.6 mol | 7 min/18° C. | | ca 24 h/20–40° C. | 89.6 | solid |
| 6-6 | 43.9 | 5.96 g 0.75 mol | 109.3 g 0.6 mol | 7 min/21° C. | 65 min r.t. 8 min | ca. 18 h/34° C. | 94 | solid, mp = 43 C. |
| 6-7 | 44 | 5.96 g 0.75 mol | 109.3 g 0.6 mol | 19 min/23° C. | 70 min | 17 h/41–47° C. | 94.7 | solid |
| 6-8 | 43.9 | 5.96 g 0.75 mol | 109.3 g 0.6 mol | 27 min/23° C. | 38 min r.t. 8 min | 16.3 h/40° C. | 97.3 | solid |

TABLE 7

| Experiment | LiH/TSBB ratio | LiH [g], mol | TSBB [g], mol, | THF [ml] | Feed. Time/ Feed temp. | Time to Temp. | Rxn. time/ Rxn temp. | Yield (%, $^{11}$B-NMR) |
|---|---|---|---|---|---|---|---|---|
| 7-1 | 3 | 7.53 g 0.9 mol | 54.65 g 0.3 mol | 250 ml | 39 min/23 C. | 0 | 20 h | 90.7 |
| 7-2 | 2 | 5.02 g, 0.6 mol | 54.65 g 0.3 mol | 250 ml | <1 min/23 C. | 0 | 24 h/24 C. | 91.0 |
| 7-3 | 1 | 2.39 g 0.3 mol | 54.65 g 0.3 mol | 250 ml | 78 min/23 C. | ca 30 min | overnight/35 C. | 86 |
| 7-4 | 1.25 | 5.96 g 0.75 mol | 109.3 g 0.6 mol | 225 ml | 6 min/21 C. | 1 h r.t. <50 min | ca 18.5 h/35 C. | 83 |
| 7-5 | 0.5 | 2.39 g 0.3 mol | 109.3 g 0.6 mol | 250 ml | <1 min/25 C. | 2.25 h/r.t. 15 min | 1.5 h/50 C. ca. 75 h/r.t.-50 C. | 94 |

TABLE 8

| Experiment | Reactor | LiH [g], mol | TSBB [g], mol | Feed. Time/ Feed temp. | Time to Temp. | Rxn. time/ Rxn temp. | Yield (%, $^{11}$B-NMR) | Remarks |
|---|---|---|---|---|---|---|---|---|
| 8-1 | Parr | 2.39 g 0.3 mol | 54.65 g 0.3 mol | 0.5 min/22° C. | 30 min r.t. 13 min | 22.3 h/35° C. | 86.6 | |
| 8-2 | Parr | 2.39 g 0.3 mol | 54.65 g 0.3 mol | 78 min/23° C. | ca 30 min | overnight/35° C. | 86 | |
| 8-3 | Flask | 7.16 g 0.9 mol | 54.65 0.3 mol | 10 min/23° C. | ca. 40 min | overnight/50° C. | 41.6 | |
| 8-4 | Flask | 2.39 g, 0.3 mol | 54.65 0.3 mol | 55 min/24° C. | 0 | ca. 24 h/r.t. | 42 | LiH added to TSBB |

TABLE 9

| Exp. No. | Reactor | LiH [g], mol, eq | TSBB [g], mol, eq | Feed. Time/ Feed temp. | Time to Temp. | Rxn. time/ Rxn temp. | Yield (%, $^{11}$B-NMR) |
|---|---|---|---|---|---|---|---|
| 9-1 | Parr reactor | 2.39 g 0.3 mol | 54.65 g 0.3 mol | 16 min/55° C. | 0 | 16.5 h/54° C. | 15.8% |
| 9-2 | Parr reactor | 2.39 g 0.3 mol | 54.65 g 0.3 mol | 12 min/55 | 0 | 17 h/55° C. | 18.3% |
| 9-3 | Parr reactor | 2.39 g, 0.3 mol | 54.65 0.3 mol | 10 min/51–55° C. | 0 | 17.5 h/52° C. | 10.3% |
| 9-3 | Morton flask | 3.14 g, 0.375 mol | 54.65 0.3 mol | <1 h/42° C. | 0 | 18 h/43° C. 24 h/34° C. | 60.8% 60.4% |
| 9-3 | Morton flask | 3.14 g, 0.375 mol | 54.65 0.3 mol | <min/34° C. | 0 | 18 h/34° C. 24 h/34° C. | 85.5% 86.3% |

TABLE 9-continued

| Exp. No. | Reactor | LiH [g], mol, eq | TSBB [g], mol, eq | Feed. Time/ Feed temp. | Time to Temp. | Rxn. time/ Rxn temp. | Yield (%, ¹¹B-NMR) |
|---|---|---|---|---|---|---|---|
| 9-4 | Parr reactor | 3.14 g 0.375 | 54.65 g 0.3 mol 19.5 wt % | 1 min/24° C. | 40 min 30 min | 1 h/35° C. 2 h/50° C. 17.5 h/50° C. | 0% 23.6% 79.3% |
| 9-5 | Zipperclave | 31.57 g 3.97 mol | 578.54 g 3.176 mol | 43 min/23° C. | 25 min | 20 h/35° C. | 86.2% |
| 9-6 | Parr reactor | 3.14 g 0.375 mol | 54.65 0.3 mol | 48 min/20° C. | 0 | 5.5 h/20° C. 22 h/20–26° C. | 74% 88.8% |
| 9-7 | Morton Flask | 3.14 g, 0.375 mol | 54.65 g 0.3 mol | 1 min/16° C. | 15 min | 18 h/14° C. ca. 24 h/30– 35° C. ca. 44 h/30– 35° C. | 0% 60.3% 62.2% |
| 9-8 | Morton flask | 3.14 g 0.375 mol | 54.65 0.3 mol | <1 min/3–5° C. | 0 | 18 h/1–5° C. | 0% |

Synthesis of Trisubstituted Borohydride Compounds Via in situ Preparation of Lithium Hydride As discussed above, n-butyl lithium (n-BuLi) slowly thermally decomposes by evolution of 1-butene and precipitation of LiH. The generation of LiH from n-BuLi is more efficient by hydrogenation of n-BuLi in the presence of an amine catalysts such as tetramethylethylenediamine (TMEDA) under the following reaction:

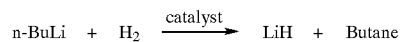

$$\text{n-BuLi} + \text{H}_2 \xrightarrow{\text{catalyst}} \text{LiH} + \text{Butane}$$

Although, it has been reported that LiH produced by this method with one equivalent of TMEDA was of sufficient reactivity to react with tri-sec-butyl borane to generate tri-sec-butyl borohydride, the present inventors have found that TMEDA, even when used in catalytic amounts, imparts impurities in the lithium trisubstituted borohydride which are detrimental to the intended usage thereof.

Hydrogenation of 10M n-BuLi in hexanes is very slow without a catalyst and does not hydrogenate rapidly with even 0.1 mole equivalent of TMEDA. At this high concentration, the n-BuLi exists as complex oligomers, hexamers, etc., which further reduce the reactivity towards hydrogenation. At 100 psig hydrogen and 60° C., 5M n-BuLi appeared to slowly take up hydrogen without TMEDA. The pressure drop was 5 psi/6 min. at 60° C. compared to 25 psi/6 min. at 55° C. and 0.1 equiv. of TMEDA (both reactions at 100 psig). However, a better method for hydrogenation of n-BuLi to complete the reaction in a short time and obtain high purity LiH is desirable.

In one literature report, n-BuLi in benzene was hydrogenated in the presence of THF, but conditions, yield and purity were not stated. *J. Am Chem. Soc.*, 23, 5668–5670 (1966). However, it is well known that n-butyl lithium will deprotonate tetrahydrofuran at room temperature to give ethylene and the lithium enolate of acetaldehyde. See, for example, *J. Org. Chem.*, 37, 560–562 (1973).

The present inventors have discovered that at a moderately low temperature, n-butyl lithium can be hydrogenated in THF without a catalyst such as TMEDA and without concurrent deprotonation of THF to give a highly pure and reactive LiH. The "activated" LiH reacts readily with hindered or highly hindered substituted boranes. The activated LiH will, for example, react completely when excess tri-sec-butyl borane (0.1 to 5%) is added.

In the present studies, THF was used either as the bulk solvent for the reaction or about two equivalents to promote hydrogenation of n-BuLi. The THF served to break up the hexamers of n-BuLi into tetramers, dimers or possibly solvated monomers facilitating hydrogenation. In a typical reaction THF was added to the n-BuLi and the mixture subjected to hydrogen until the hydrogenation was complete.

Temperature and mode of addition were found to be important variables. The hydrogen pressure was also evaluated to confirm the increased hydrogen up-take at a higher hydrogen pressure.

Temperature and Mode of Addition: A large exotherm (about 20 to 30° C.) was observed upon addition of THF to the n-BuLi/hexane solution. It is believed that the exotherm is a result of solvation of the n-BuLi by THF and not a result of deprotonation of THF. In several experiments the exotherm of the reaction took the solution temperature up in the range of 20 to 24° C. for a short period (see Addition $T_{max}$ in Table 1, Experiment Nos. 2 and 3) but no THF deprotonation impurities were observed by IR.

TABLE 10

| Exp. No. | THF Temp (° C.) | n-BuLi Temp | Addition $T_{max}$ | $H_2$ Rxn Temp | Mode of Addition | % mole n-BuLi deprotonation |
|---|---|---|---|---|---|---|
| 10-1 | −20 | −20 | 3 | −10 to −15 | A | None |
| 10-2 | −20 | −20 | 21 | −20 | A | None |
| 10-3 | −78 | −8 | 24 | −8 | A | None |
| 10-4 | −30 | −16 | 25 | −20 | A | 0.7 |
| 10-5 | −78 | 0 | −3 | −15 to −20 | B | 0.6 |
| 10-6 | −28 | 0 | −12 | −15 to −20 | B | 0.8 |
| 10-7 | −20 | 0 | −9 | −15 to −20 | C | 0.7 |
| 10-8 | −20 | −20 | −9 | 0 | A | 0.7 |

TABLE 10-continued

| Exp. No. | THF Temp (° C.) | n-BuLi Temp | Addition T$_{max}$ | H$_2$ Rxn Temp | Mode of Addition | % mole n-BuLi deprotonation |
|---|---|---|---|---|---|---|
| 10-9 | 0 | 0 | 9 | 0 | A | 0.8 |
| 10-10 | 22 | 0 | 15 | 0 | A | 1.8 |
| 10-11 | −20 | 0 | −11 | −15 | C | 2.8 |

In the studies of Table 10, the Mode of Addition describes reactions in which: A represents that THF was added to n-BuLi in the reactor; B represents simultaneous addition of both THF and n-BuLi to the reactor, and C represents the addition of n-BuLi to THF in the reactor. T$_{max}$ was the maximum temperature of the mixture as a result of the reaction exotherm. The percent n-BuLi deprotonation was measured by infrared spectroscopy and represents the mole % n-BuLi that reacted with THF. For example, 0.7 indicates that of the contained n-BuLi, 99.3% could (and was) converted to LiH but 0.7 mole % deprotonated THF, generating a lithium enolate impurity.

n-BuLi (10M) appears to freeze at a temperature between approximately −13 and approximately −16° C., so cooling of 10M n-BuLi is preferably limited to between approximately 0 and approximately −10° C. The three modes of addition set forth in Table 10 all gave highly reactive lithium hydride with low levels of impurities. The preferred mode of addition, however, is addition of chilled THF to chilled n-BuLi (Addition Mode A). The temperature during hydrogenation was kept preferably between −20 and 0° C. in the reactions of Table 10.

Addition Mode A gave the best results (Table 10, Experiment Nos. 10-1 through 10-3) in that no deprotonation of THF was observed in most experiments. In six other examples <1% of the n-BuLi deprotonated THF. With about 2 equivalents of THF and reaction temperatures of 0° C., our results (Table 10, Experiment Nos. 10-9 and 10-10) show that THF deprotonation occurred to a limited extent. By IR, the amount of n-BuLi that had deprotonated THF is between approximately 0.5% and approximately 2%.

In Addition Mode B, dropping the THF temperature from approximately −20 to approximately −78° C. (Table 10, Experiments 10-5 and 10-6 respectively) did not significantly decrease the amount of THF deprotonation.

In Addition Mode C, in which n-BuLi was added to cold THF (Experiment Nos. 10-7 and 10-11), the deprotonation of THF was somewhat larger. Although, Addition Mode C is the least desirable mode of addition, Experiment No. 10-7 resulted in less than 1% THF deprotonation.

Effect of hydrogen pressure: Most reactions were left overnight under hydrogen to ensure complete hydrogenation. A direct comparison of hydrogenation time cannot be made, however, because, leaks in the system made the endpoint indefinite. The rate of hydrogen uptake at 35–40 psig and 0° C. is approximately the same as experienced when using 0.1 equiv. of TMEDA and 40 psig hydrogen at room temperature (about 4 hours for 0.64 mole n-BuLi). At −20° C., the hydrogenation took 6–8 hours at 35 psig hydrogen. As expected, the hydrogenation at 100 psig (−8° C.) was rapid and was complete in about 1.5 hours.

Effect of reaction temperature on the TSBB reaction: The reaction of the LiH slurry with TSBB was rapid and exothermic. The TSBB can be added over a short period (for example, over a 10 min. period) where the exotherm brings the reaction temperature to 50° C. with no detrimental effects. When the TSBB was added slowly (for example, over a 1 h period), the reaction temperature held in the range (22–33° C.) and the conversion to lithium tri-sec-butylborohydride was excellent.

Reaction of LiH in Hydrocarbon Solvents: A test was performed to examine whether the reactivity was a result of solvent or particle size/reactivity. In that regard, LiH produced in a batch which had a high concentration of lithium enolate was filtered with a medium glass frit. The active hydrogen titration showed this off-white solid to be approximately 54.82% lithium hydride. Analysis by GC/MS allowed estimation of the residual THF at approximately 6–7%. Presumably, the remaining material is hydroxide, oxide and lithium enolate. This LiH was used in a test to determine the reactivity of LiH produced from n-BuLi.

Table 11 lists the results of reactions in monoglyme (M1M), toluene, hexane and heptane. In these studies, a two-fold molar excess tri-sec-butylborane was added to the LiH. After overnight stirring, only the M1M sample showed appreciable conversion to lithium tri-sec-butylborohydride. The hydrocarbon solvent mixtures were heated at 40° C. and reanalyzed which showed no further change. Finally, to determine if addition of THF would promote the conversion to lithium tri-sec-butylborohydride, about one equivalent of THF relative to the LiH was added to the sample. Conversion of about 30% relative to the total amount of active LiH was observed after stirring 24 h at ambient temperature. Heating the mixtures increased the conversion up to 56% for the hexane solution. The amount of conversion seen in these hydrocarbon solvents was directly related to the amount of THF in the solution. The initial conversion amounts observed reflect the residual THF in the filtered LiH.

TABLE 11

| Exp. No. | LiH g crude mmol active | TSBB g and mmol | Solvent grams | mol % conv. after RT overnight | Mol % conv. of LiH after 6 h at 40° C. | Mol % of LiH conv. after 1 eq. THF | Mol % conv. of LiH after 6 h 40–50° C. |
|---|---|---|---|---|---|---|---|
| 11-1 | 1.05 g 72 mmol | 18 g 100 mmol | M1M 76 g | 58.4 | NA | NA | NA |
| 11-2 | 0.94 g 64 mmol | 18 g 100 mmol | hexane 76 g | 5.5 | No change | 33 | 56 |
| 11-3 | 0.95 g 65 mmol | 18 g 100 mmol | heptane 76 g | 11 | No change | 32 | 30 |
| 11-4 | 0.8 g 55 mmol | 18 g 100 mmol | toluene 76 g | 5.2 | No change | 33 | 44 |

Reaction of the LiH with Hindered Trialkylboranes:

Commercial LiH is typically not of sufficient reactivity to react with highly hindered trisubstituted boranes such as Alpine-Borane® or trisiamylborane. Lithium hydride produced from n-butyl lithium, however, was discovered to be much more reactive. Reaction of both R-Alpine-Borane® and trisiamylborane with the reactive LiH of the present invention gave the corresponding borohydride compounds, R-Alpine-Hydride® and trisiamylbbrohydride, respectively. After 24 hours at ambient temperature the conversion to R-Alpine-Hydride® was nearly quantitative. The identity of the R-Alpine-Hydride® was confirmed by addition of t-BuLi in pentane to R-Alpine-Borane®. The reaction of LiH with trisiamylborane was slower, only 16% conversion after 20 h at ambient temperature and 29% conversion after 48 h.

Activated lithium hydride can thus be produced from the hydrogenation of n-BuLi in THF without the use of an amine catalyst. Reagents synthesized using such LiH are of greater purity than those synthesized with LiH produced with the use of even catalytic amounts of amine catalysts such as TMEDA. Preferably, cold THF is added to cold n-BuLi (preferably, in a temperature range of approximately 0 to approximately –20° C.). The reaction temperature during the hydrogenation is preferably maintained in a range of approximately 0 to approximately –20° C. Preferably, hydrogen uptake and the disappearance of n-BuLi are monitored.

In the synthesis of lithium tri-sec-butylborohydride from the activated LiH of the present invention, the addition rate of TSBB (one equivalent) is preferably maintained such that the temperature is less than 55° C.

EXAMPLES
Synthesis of Sterically Hindered Trisubstituted Borohydride Reagents from Commercially Available Lithium Hydride

Example 1

(Experiment 1-6)

To an open Zipperclave reactor tetrahydrofuran (1730 g) and a slurry of lithium hydride (31.57 g) in tetrahydrofuran (400 g) were charged. The reactor vessel was closed and connected to a nitrogen manifold. The system was purged several times with nitrogen gas. From a glass pressure vessel tri-sec-butylborane (578.54 g) was added subsurface to the stirred reaction mixture over 43 min at approximately 22° C. The reactor was placed under 10 psig nitrogen pressure and heated to about 32° C. in 24 min. After stirring at 1500 rpm for about 20 h at approximately 33–35° C. a sample of the reactor content was taken and analyzed by $^{11}$B-NMR. Integration of the $^{11}$B-NMR signals showed 86.2% lithium tri-sec-butylborohydride ($\delta$=–7.2 ppm) and 13.8% tri-sec-butylborane ($\delta$=85.7 ppm). The reaction mixture was cooled to 17° C. then filtered through a Balston filter cartridge (Grade 100-25 BQ) and analyzed for base and hydride content.

Example 2

(Experiment 2-1)

In a glovebox, lithium hydride powder (2.39 g) and tetrahydrofuran (250 ml) were charged to a Parr pressure reactor. The reactor vessel was closed, placed into the heater/stirrer mechanism and connected to a nitrogen manifold. The system was purged three times with hydrogen gas. The reaction mixture was heated to 55° C., then tri-sec-butylborane (54.65 g) was added from a glass pressure vessel to the headspace of the stirred reaction mixture within 16 min. The Parr reactor was placed under 20 psig hydrogen pressure. After stirring overnight at about 54° C. a sample of the reactor content was taken and analyzed by $^{11}$B-NMR. Integration of the $^{11}$B-NMR signals showed 15.8% lithium tri-sec-butylborohydride ($\delta$=–5.84 ppm) and 84.2% tri-sec-butylborane ($\delta$=86.1 ppm).

Example 3

(Experiment 2-11)

In a glovebox, lithium hydride powder (2.39 g) and tetrahydrofuran (250 ml) were charged to a Parr pressure reactor. The reactor vessel was closed, placed into the heater/stirrer mechanism and connected to a nitrogen manifold. The system was purged twice with nitrogen gas. From a glass pressure vessel tri-sec-butylborane (54.65 g) was added to the headspace of the stirred reaction mixture within 10 min. The Parr reactor was placed under 5 psig nitrogen pressure and then heated to approximately 52° C. within 25 min. After stirring for 23 h at 52° C. a sample of the reactor content was taken and analyzed by $^{11}$B-NMR. Integration of the $^{11}$B-NMR signals showed 80.4% lithium tri-sec-butylborohydride ($\delta$=–7.52 ppm) and 19.6% tri-sec-butylborane ($\delta$=85.9 ppm).

Example 4

(Experiment 3-2)

In a glovebox, tri-sec-butylborane (63.76 g) and tetrahydrofuran borane complex (1 M, 21.78 g) were placed in a bottle. The mixture was allowed to equilibrate overnight giving tri-sec-butylborane of about 85% purity by $^{11}$B-NMR.

The material was placed in a glass pressure vessel. Lithium hydride (3.14 g) and tetrahydrofuran (250 ml) were charged to a Parr pressure reactor. The reactor vessel was closed, placed into the heater/stirrer mechanism and connected to a nitrogen manifold. The system was purged four times with nitrogen gas. From the glass pressure vessel the low purity tri-sec-butylborane (73.31 g) was added to the headspace of the stirred reaction mixture over 52 min at approximately 26° C. The Parr reactor was placed under 15 psig nitrogen pressure and then stirred overnight at approximately 27° C. The reactor content was sampled and analyzed by $^{11}$B-NMR. Integration of the $^{11}$B-NMR signals showed lithium tri-sec-butylborohydride yield of about 17% ($\delta$=−7.05 ppm).

Example 5

(Experiment 3-4)

In a glovebox, lithium hydride powder (3.84 g, purity 77.7%) and tetrahydrofuran (250 ml) were charged to a Parr pressure reactor. The reactor vessel was closed, placed into the heater/stirrer mechanism and connected to a nitrogen manifold. The system was purged four times with nitrogen gas. From a glass pressure vessel tri-sec-butylborane (54.65 g) was added to the headspace of the stirred reaction mixture over 54 min. The Parr reactor was placed under 20 psig nitrogen pressure. After stirring overnight at approximately 25° C. a sample of the reactor content was taken and analyzed by $^{11}$B-NMR. Integration of the $^{11}$B-NMR signals showed about 3% lithium tri-sec-butylborohydride ($\delta$=−5.8 ppm) and about 97% tri-sec-butylborane ($\delta$=85.3 ppm).

Example 6

(Experiment 4-2)

In a glovebox, lithium hydride powder (2.39 g, purity 99.1%) and tetrahydrofuran (250 ml) were charged to a Morton flask. The flask was closed, placed into an oil bath and connected to a nitrogen manifold. Tri-sec-butylborane (54.65 g) was added from a glass pressure vessel over 10 min to the headspace of the reaction mixture at ambient temperature (approximately 24° C.). The reaction mixture was heated to about 50° C. within an hour. After stirring overnight the reaction mixture was allowed to cool to ambient temperature and then analyzed by $^{11}$B-NMR. Integration of the $^{11}$B-NMR signals showed 28.5% lithium tri-sec-butylborohydride ($\delta$=−6.87 ppm, singulett) and 71.5% tri-sec-butylborane ($\delta$=85.8 ppm).

Example 7

(Experiment 4-6)

In a glovebox, lithium hydride powder (2.51 g, purity 95%) and tetrahydrofuran (207.8 g) were charged to a Morton flask. The flask was closed, placed into an oil bath and connected to a nitrogen manifold. The reaction mixture was heated to approximately 30° C. then tri-sec-butylborane (62.85 g) was added from a glass pressure vessel within 1 min. After stirring for 24 h at approximately 30° C. to approximately 38° C. a sample of the reactor content was taken and analyzed by $^{11}$B-NMR. Integration of the $^{11}$B-NMR signals showed 63.4% lithium tri-sec-butylborohydride ($\delta$=−6.37 ppm) and 36.6% tri-sec-butylborane ($\delta$=86.8 ppm), which corresponds to a lithium tri-sec-butylborohydride yield of 72.9%.

Example 8

(Experiment 5-4)

In a glovebox, lithium hydride powder (3.14 g, purity 96.4%) and tetrahydrofuran (250 ml) were charged to a Parr pressure reactor. The reactor vessel was closed, placed into the heater/stirrer mechanism and connected to a nitrogen manifold. The system was purged four times with nitrogen gas then heated to approximately 53° C. and stirred overnight. The next day the reaction mixture was cooled to approximately 23° C. and the reactor pressure lowered to ambient pressure. From a glass pressure vessel tri-sec-butylborane (54.65 g) was added to the stirred reaction mixture over 89 min. The Parr reactor was placed under nitrogen pressure. After stirring for 21 h at approximately 23° C. to approximately 27° C. a sample of the reactor content was taken and analyzed by $^{11}$B-NMR. Integration of the $^{11}$B-NMR signals showed 84.8% lithium tri-sec-butylborohydride ($\delta$=−7.3 ppm) and 15.2% tri-sec-butylborane ($\delta$=85.7 ppm).

Example 9

(Experiment 6-8)

In a glovebox, lithium hydride powder (5.96 g) and tetrahydrofuran (150 ml) were charged to a Parr pressure reactor. The reactor vessel was closed, placed into the heater/stirrer mechanism and connected to a nitrogen manifold. The system was purged with nitrogen gas. From a glass pressure vessel tri-sec-butylborane (109.3 g) was added to the stirred reaction mixture within 27 min. The Parr reactor was placed under 10 psig nitrogen pressure, stirred for 38 min at approximately 23° C. and then heated to approximately 40° C. After stirring overnight at 40° C. the reactor was taken to the glovebox. The reactor was opened and a sample of the solid reactor content dissolved in THF. The sample was analyzed by $^{11}$B-NMR showing 97.4% lithium tri-sec-butylborohydride ($\delta$=−7.32 ppm).

Example 10

(Experiment 7-2)

In a glovebox, lithium hydride powder (5.02 g) and tetrahydrofuran (250 ml) were charged to a Parr pressure reactor. The reactor vessel was closed, placed into the heater/stirrer mechanism and connected to a nitrogen manifold. The system was purged twice with nitrogen gas. From a glass pressure vessel tri-sec-butylborane (54.65 g) was added to the stirred reaction mixture within 1 min. The Parr reactor was placed under 10 psig nitrogen pressure. After stirring for 24 h at ambient temperature a sample of the reactor content was taken and analyzed by $^{11}$B-NMR. Integration of the $^{11}$B-NMR signals showed 91% lithium tri-sec-butylborohydride ($\delta$=−7.32 ppm) and 9% tri-sec-butylborane ($\delta$=86.2 ppm).

Example 11

(Experiment 8-2)

In a glovebox, lithium hydride powder (2.3 g) and tetrahydrofuran (250 ml) were charged to a Parr pressure reactor. The reactor vessel was closed, placed into the heater/stirrer mechanism and connected to a nitrogen manifold. The system was purged with nitrogen gas. From a glass pressure vessel tri-sec-butylborane (54.65 g) was added to the stirred reaction mixture over 78 min at approximately 23° C. The Parr reactor was placed under 10 psig nitrogen pressure, stirred for 25 min at approximately 23° C., then heated to approximately 35° C. After stirring overnight at 35° C. a sample of the reactor content was taken and analyzed by $^{11}$B-NMR. Integration of the $^{11}$B-NMR signals showed 86% lithium tri-sec-butylborohydride ($\delta$=−7.97 ppm) and 14% tri-sec-butylborane ($\delta$=85.2 ppm).

Example 12

(Experiment 8-4)

In a glovebox, tri-sec-butylborane (54.65 g) and tetrahydrofuran (250 ml) were charged to a Morton flask. The flask was closed and transferred to a hood. The flask was equipped with an addition funnel for solids and connected to a nitrogen manifold. The system was purged with nitrogen gas. Then lithium hydride (2.39 g) was charged over 55 min to the stirred reaction mixture at approximately 24° C. The reaction mixture was stirred for 5.5 h, then allowed to sit overnight at ambient temperature. A sample of the reactor content was taken and analyzed by $^{11}$B-NMR. Integration of the $^{11}$B-NMR signals showed 42% lithium tri-sec-butylborohydride ($\delta$=−7.16 ppm) and 58% tri-sec-butylborane ($\delta$=85.9 ppm).

Example 13

In a glovebox lithium hydride powder (3.01 g) and tetrahydrofuran (170 ml) were charged to a Parr pressure reactor. The reactor vessel was closed, placed into the heater/stirrer mechanism and connected to a nitrogen manifold. The system was purged four times with nitrogen gas. From a glass pressure vessel B-hexyl-9-borabicyclo[3.3.1]nonane in THF (183.4 g, 1.38M) was added to the stirred reaction mixture over 50 min. The Parr reactor was placed under 20 psig nitrogen pressure. After stirring for about 17.5 h at 26° C. a sample of the reactor content was taken and analyzed by $^{11}$B-NMR. The $^{11}$B-NMR signals showed lithium B-hexyl-9-boratabicyclo[3.3.1]nonane $\delta$=−12.05 ppm) as the only component. Infrared spectroscopy R showed the typical BH peak at 2048 cm$^{-1}$.

Example 14

In a glovebox lithium hydride powder (3.14 g) and tetrahydrofuran (120 ml) were charged to a Parr pressure reactor. The reactor vessel was closed, placed into the heater/stirrer mechanism and connected to a nitrogen manifold. The system was purged four times with nitrogen gas. From a glass pressure vessel B-cyclohexyl-9-borabicyclo[3.3.1]nonane in THF (177.5 g, 34.5wt %) was added to the stirred reaction mixture over 62 min. The Parr reactor was placed under 20 psig nitrogen pressure. After stirring for about 20 h at 26 to 29° C. a sample of the reactor content was taken and analyzed by $^{11}$B-NMR. Integration of the $^{11}$B-NMR signals showed about 72% lithium B-cyclohexyl-9-boratabicyclo[3.3.1]nonane ($\delta$=−10.16 ppm). The reactions of Examples 13 and 14 are illustrated below.

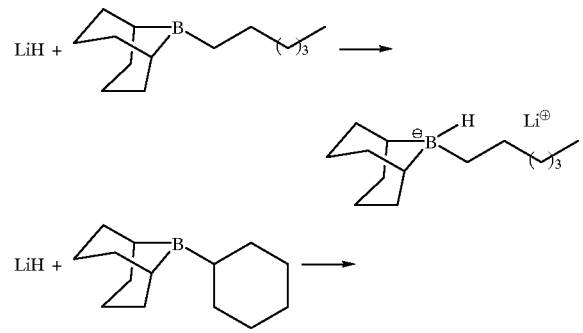

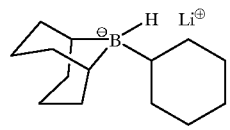

Synthesis of Sterically Hindered Trisubstituted Borohydride Compounds Via in situ Preparation of Lithium Hydride The following general discussion of apparatus, methods and physical properties apply to Examples 13 through 19.

Experimental Apparatus: Reactions were performed in a glass low pressure reactor under hydrogen pressures of approximately 35–40 psig and in a stainless steel Parr reactor at approximately 100 psig. When the reactions were not under hydrogen, nitrogen was used as a cover gas.

Analytical Methods

Titration of n-butyl lithium: n-Butyl lithium was titrated using 1,10-phenanthroline as an indicator. Reproducible results were obtained. This method can also be used to determine the extent of hydrogenation and hydrogenation endpoint.

Rate of hydrogenation: The rate of hydrogenation in the glass low pressure reactor was roughly estimated by measuring the bubble count versus time as the hydrogen was drawn into the reaction vessel. In the Parr vessel, the pressure drop was monitored and hydrogen was added when the hydrogen pressure had dropped from approximately 100 psig to approximately 75–80 psig. A good indicator of the complete hydrogenation was reduced or no uptake of hydrogen.

Extent of THF decomposition: The lithium enolate of acetaldehyde (LiOCHCH$_2$) can be detected by a peak at 1612 cm$^{-1}$ in the IR spectrum. Quantitative measurement of the peak at 1612 cm$^{-1}$ was used to determine the extent of THF deprotonation by n-BuLi.

Physical Properties

LiH: The lithium hydride produced by the hydrogenation of n-BuLi was a fine white to cream solid that very slowly settled from solution.

Lithium tri-sec-butylborohydride pyrophoricity: By the Department of Transportation pyrophoricity test, the lithium tri-sec-butylborohydride solutions produced in THF (containing residual hexanes) were non-pyrophoric even with 2 mole % TSBB present. Because this compound is a borderline pyrophoric liquid by this test, however, it should be handled as a pyrophoric liquid, especially in light that inadvertent spilling and mixing with water could increase the pyrophoricity.

Hydrogenation of n-BuLi in THF:

Example 15

Addition Mode A: THF was added to the n-BuLi. n-BuLi (60 ml of 10M) was placed in a glass low pressure reactor and cooled to approximately −16° C. THF (775 g) was placed in a Fisher-Porter bottle and chilled to approximately −20° C. THF was added to the n-BuLi over about 20 minutes. The solvation reaction was exothermic causing the mixture to rise in temperature up to approximately 25° C. midway through the THF addition. Hydrogen was introduced to the vessel at approximately 35 psig. The reactor was kept at approximately −15 to approximately −20° C. during the hydrogenation period of 8 hours. An IR spectrum of a filtered sample of the slurry showed a small peak at 1620 cm$^{-1}$ for the lithium enolate of acetaldehyde; calculated amount of deprotonation was 0.7 mol %. The LiH slurry was removed to a round-bottomed flask after the hydrogen uptake ceased.

Example 16

Addition Mode B: THF and n-BuLi were added simultaneously to a glass low pressure reactor with the liquids hitting the impeller blades. THF (409 g) and n-BuLi (60 ml of 10M) were placed in separate Fisher Porter bottles and chilled to approximately −28° C. and approximately 0° C., respectively. The reactor was placed in a −30° C. bath. During the simultaneous addition (10 min) of the to liquids the temperature of the mixture rose to approximately −12° C. Hydrogen was introduced at approximately 35 psig and the temperature was held at approximately −20° C. during the hydrogenation period of about 8 hours. An IR spectrum of a filtered sample of the slurry showed a small peak at 1612 $cm^{-1}$ for the lithium enolate of acetaldehyde; calculated amount of deprotonation was 0.8 mol %.

Example 17

Addition Mode C: n-BuLi was added to the THF. THF (409 g) was placed in a glass low pressure reactor and cooled to approximately −20° C. n-BuLi (60 ml of 10M) was placed in a Fisher-Porter bottle and chilled to approximately 0° C. n-BuLi was added to the THF over about 15 minutes. The salvation reaction was exothermic, causing the mixture to rise in temperature up to approximately −9° C. midway through the THF addition. Hydrogen was introduced to the vessel at approximately 35 psig. The reactor was kept at −15 to −20° C. during the hydrogenation period of 8 hours. An IR spectrum of a filtered sample of the slurry showed a small peak at 1612 $cm^{-1}$ for the lithium enolate of acetaldehyde; calculated amount of deprotonation was 0.7 mol %. The LiH slurry was quenched with methanol and discarded.

Example 18

Addition Mode A: THF was added to the n-BuLi. N-BuLi (250 ml of 2.5M) was placed in a glass low pressure reactor and cooled to approximately −20° C. Hydrogen was introduced to the vessel at approximately 35 psig. THF (493 g) was placed in a Fisher-Porter bottle and chilled to approximately −20° C. THF was added slowly to the n-BuLi to control the exotherm. The temperature during the THF addition was kept below approximately 0° C. The reactor was kept at approximately −10 to approximately −15° C. during the hydrogenation period of 8 hours. An IR spectrum of a filtered sample of the slurry showed no peak at 1620 $cm^{-1}$ for the lithium enolate of acetaldehyde. Tri-sec-butylborane (114 g, 2 mole % excess) was added to the LiH slurry at ambient temperature over 40 minutes. A six-degree exotherm during the TSBB addition was observed. The lithium hydride reacted completely with the TSBB. Final analysis of the lithium tri-sec-butylborohydride solution by base titration was 0.89M.

Example 19

Reaction of lithium hydride with R-AlpineBorane®: A portion of the LiH slurry (containing 0.44 g of LiH) from Example 1 was placed in a 100 ml round-bottomed flask with stir bar, nitrogen inlet and thermocouple. R-AlpineBorane (14.2 g) was added by syringe over 10 min. to the LiH slurry. The temperature rose from approximately 21° C. to approximately 29° C. during the addition. One hour after the addition, the reaction was 80% complete by $^{11}$B NMR spectroscopy. After 24 hours at ambient temperature the conversion to R-Alpine-Hydride was nearly quantitative. The $^{11}$B NMR spectrum showed a doublet at −6.3 ppm (J=69 Hz). Base titration indicated the solution was 36 wt % R-Alpine-Hydride®.

Example 20

Reaction of lithium hydride with trisiamylborane: A portion of the LiH slurry (containing 0.45 g of LiH) from Example 1 was placed in a 100 ml round-bottomed flask with stir bar, nitrogen inlet and thermocouple. Trisiamylborane (12.6 g) was added to the reaction flask from a Fisher-Porter tube over 1 h. to the LiH slurry. The temperature did not rise during the addition. By $^{11}$B NMR spectroscopy, the reaction of LiH with trisiamylborane showed only 16% conversion after 20 h at ambient temperature and 29% conversion after 48 h. The reaction mixture was heated at 40–45° C. for 6 hours which pushed the conversion to 40% lithium trisiamylborohydride.

The product showed two doublets in the $^{11}$B NMR at −12 and −13 ppm as was also seen by H. C. Brown. This phenomena is thought to be a result of diastereomers formed.

Example 21

Hydrogenation in the Parr vessel at 100 psig: n-BuLi (80 ml of 10M) was loaded into a stainless steel Parr reactor and chilled to approximately −8° C. THF (390 g) in a Fisher-Porter bottle was chilled in a dry ice/methanol bath (approximately −78° C.). The THF was added rapidly to the n-BuLi. The solvation reaction was exothermic, causing the mixture to rise in temperature up to approximately 24° C. midway through the THF addition. Hydrogen was introduced at approximately 100 psig, and the temperature was held between approximately −8° C. and approximately −10° C. during the hydrogenation period of about 1.5 hours. An IR spectrum of a filtered sample of the slurry showed no peak at 1612 $cm^{-1}$ for the lithium enolate of acetaldehyde.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of synthesizing LiH, LiD or LiT comprising the step of reacting without an amine catalyst an alkyl lithium with hydrogen, deuterium or tritium in the presence of tetrahydrofuran, the reaction temperature being maintained in the range of approximately −78° C. to approximately 20° C.

2. The method of claim 1 wherein the alkyl lithium is n-butyl lithium.

3. The method of claim 2 wherein the temperature is maintained in the range of approximately −30° C. to approximately 0° C.

4. The method of claim 2 wherein the temperature is maintained in the range of approximately −20° C. to approximately 0° C.

5. The method of claim 2 wherein the temperature is maintained in the range of approximately −15° C. to approximately −5° C.

6. The method of claim 2 wherein chilled tetrahydrofuran is added to chilled n-butyl lithium.

7. The method of claim 6 wherein the tetrahydrofuran is chilled to a temperature in the range of approximately −78° C. to approximately 20° C.

8. The method of claim 7 wherein tetrahydrofuran is chilled to a temperature in the range of approximately −30° C. to approximately 0° C.

9. The method of claim 7 wherein the tetrahydrofuran is chilled to a temperature in the range of approximately −20° C. to approximately 0° C.

10. The method of claim 7 wherein the tetrahydrofuran is chilled to a temperature in the range of approximately −10° C. to approximately −5° C.

11. The method of claim 7 wherein the n-butyl lithium has approximately a 10M concentration and is chilled to a temperature in the range of approximately −10° C. to approximately 0° C.

12. The method of claim 2 wherein the reaction temperature being maintained in the range of approximately −20° C. to approximately −10° C.

13. A method of synthesizing LiH, LiD or LiT comprising the step of reacting without an amine catalyst an alkyl lithium with hydrogen, deuterium or tritium in the presence of tetrahydrofuran, the reaction temperature being maintained in the range of approximately −78° C. to approximately 0° C.

14. The method of claim 13 wherein the alkyl lithium is n-butyl lithium.

15. The method of claim 13 wherein the temperature is maintained in the range of approximately −30° C. to approximately 0° C.

16. The method of claim 13 wherein the temperature is maintained in the range of approximately −20° C. to approximately 0° C.

17. The method of claim 13 wherein the temperature is maintained in the range of approximately −15° C. to approximately −5° C.

18. The method of claim 14 wherein the n-butyl lithium is chilled.

19. The method of claim 18 wherein chilled tetrahydrofuran is added to the chilled n-butyl lithium.

20. The method of claim 19 wherein the tetrahydrofuran is chilled to a temperature range of approximately −78° C. to approximately 20° C.

* * * * *